United States Patent
Rubinsky

[11] Patent Number: 6,041,787
[45] Date of Patent: Mar. 28, 2000

[54] USE OF CRYOPROTECTIVE AGENT COMPOUNDS DURING CRYOSURGERY

[76] Inventor: Boris Rubinsky, 1619 Sonoma Ave., Albany, Calif. 94707

[21] Appl. No.: 09/042,834

[22] Filed: Mar. 17, 1998

Related U.S. Application Data

[60] Provisional application No. 60/040,854, Mar. 17, 1997.

[51] Int. Cl.[7] .................................................. A61B 17/36
[52] U.S. Cl. ............................. 128/898; 606/20; 606/21; 606/23
[58] Field of Search ....................... 606/20–26; 128/898, 128/DIG. 27

[56] References Cited

U.S. PATENT DOCUMENTS

| | | | |
|---|---|---|---|
| 3,786,814 | 1/1974 | Armao | 606/23 |
| 4,664,110 | 5/1987 | Schanzlin | 606/20 |
| 5,571,801 | 11/1996 | Segall et al. | 514/59 |
| 5,603,221 | 2/1997 | Maytal | 65/51.2 |
| 5,654,279 | 8/1997 | Rubinsky et al. | 606/20 |
| 5,741,248 | 4/1998 | Stern et al. | 606/23 |
| 5,833,685 | 11/1998 | Tortal et al. | 606/25 |

FOREIGN PATENT DOCUMENTS

| | | |
|---|---|---|
| WO 96/36293 | 11/1996 | WIPO . |
| WO 96/37158 | 11/1996 | WIPO . |

*Primary Examiner*—Lee Cohen
*Attorney, Agent, or Firm*—Testa, Hurwitz & Thibeault, LLP

[57] ABSTRACT

The invention features an apparatus and method for protecting tissue from freeze damage during cryosurgery. According to the method, a cryoprotective agent is introduced to a tissue to be protected in an amount sufficient to protect the tissue from damage during cryosurgery, and cryosurgery is performed on tissue to be destroyed.

10 Claims, 3 Drawing Sheets

USE OF CRYOPROTECTIVE AGENT COMPOUNDS DURING CRYOSURGERY

RELATED APPLICATIONS

This application claims priority to provisional application U.S.S. No. 60/040,854 filed Mar. 17, 1997.

FIELD OF THE INVENTION

The invention relates to cryosurgery and, more specifically, relates to an apparatus and method for protecting tissue from damage during cryosurgery.

BACKGROUND OF THE INVENTION

Cryosurgery is a procedure for destroying tissue. In cryosurgery, undesirable tissues are frozen and destroyed. The technique is minimally invasive, usually requiring an insertion of one or more thin, cylindrical, cryosurgical probes into the undesirable tissue. The probes are cooled internally with a cryogen and are insulated except at the tip. The uninsulated tip is inserted in a tumor or other undesirable tissue, and the tissue is frozen from the probe surface outward. When the desired amount of tissue has been frozen, cryogen is prevented from flowing to the probe, and the tissue is allowed to thaw. After cryosurgery, the frozen tissue is left in situ to be reabsorbed by the immune system over time.

Since freezing originates from the small uninsulated tip of a probe, cryosurgery can be confined to a region of the diseased tissue, thereby sparing surrounding healthy tissue. The freezing process can be precise and controlled, as the freezing interface is sharp and propagates slowly (in the order of mm/min). A small probe having a diameter of around 3 mm can produce a 3.5 cm ice ball, and therefore treat a relatively large tissue region. When the shape of the pathological tissue is large and complex, several probes can be used simultaneously to generate a frozen region of a desired shape. For example, prostate and liver cryosurgery is currently performed with five 3 mm diameter probes. Multiple sites can be treated separately or together. Because the only physical invasion of the tissue is the insertion of the cryoprobes, cryosurgery does not create a lot of complications, and patient morbidity is low. Cryosurgery can produce excellent medical results with less distress and disfiguration at a lower cost. In addition, cryosurgery is not dose limited, therefore retreatment is possible.

Until recently, a major impediment to the extensive use of cryosurgery on internal tissues has been the inability to observe the frozen region deep inside the body, which could cause complications of over or under freezing. Breakthroughs in non-invasive imaging technology, however, have made possible major advances in cryosurgery in general, and prostate and liver cryosurgery in particular. Intraoperative ultrasound can image the process of freezing during cryosurgery by virtue of the fact that the interface between frozen tissue and non-frozen tissue is associated with a change in acoustic impedance that reflects ultrasound waves. Cryosurgery is now almost universally carried out under ultrasound guidance. Another recent improvement in imaging technology for use with cryosurgery is magnetic resonance imaging. This technique, which images the process of freezing in three dimensions, can monitor the freezing interface with a resolution of 200 micrometer, and can control its shape through magnetic resonance feedback. Additional methods of imaging are being continuously developed. One such method under development is the use of light to image freezing. Cryosurgery can be performed with greater accuracy and control with the assistance of the imaging techniques. Therefore, cryosurgery is gaining acceptance as a first-line therapy for prostate, liver and other cancer therapy.

While advances in imaging have provided the means to accurately monitor and control the extent of freezing during cryosurgery, the ability to image the extent of freezing have revealed the existence of new problems. The problems relate to the fact that during cryosurgery, healthy tissues, nerves, or blood vessel are being frozen either accidentally or because of constrains in the placement of cryosurgical probes. For example, destruction of healthy tissues or nerves can cause incontinence or impotence in prostate cryosurgery. Prostate cryosurgery typically uses five cryosurgical probes placed around the urethra. This causes an ice ball to form around the urethra. While it is desirable to freeze prostate tissue that is located close to the urethra to completely destroy a prostate tumor, the urethra itself cannot be frozen because this will induce significant complications such as sloughing and incontinence. An existing solution to this problem is to introduce a heating device in the urethra during prostate cryosurgery to protect the urethra from freezing. Similarly, it is desirable to freeze prostate tissue located close to the rectum during cryosurgery. However, freezing the rectum itself produces major complications. While rectal ultrasound monitoring has significantly reduced the probability of inadvertently freezing the rectum, situations in which the rectum is frozen accidentally still occur. It is also important not to freeze the nerve bundle which connects to the penis and passes through the prostate during prostate cryosurgery. Destruction of the nerves by freezing can lead to impotence. Therefore, surgeons are faced with the dilemma of choosing between destroying all the prostate tumors as close as possible to the nerves, while risking impotence or destroying less prostate tissue to preserve potency while risking survival of malignant tissue.

Similar problems exist with cryosurgery of other body parts. During liver or other organ cryosurgery where tumors are located close to large blood vessels, it is important to freeze the tumors as close to the blood vessels as possible, without damaging the blood vessels themselves. During brain cryosurgery, it is important to avoid freezing of regions of sensitive tissue. In cryoliposuction, there is a need for protecting the outer appearance of the skin while freezing the fatty tissue close to the skin. These examples illustrate that a challenge to cryosurgery is in protecting certain healthy tissues either within or around a malignant or unwanted tissue region, while destroying the malignant or unwanted tissue region during cryosurgery.

Much of the research on the effects of freezing on biological materials has focused on the use of freezing for preservation of cells (such as red blood cells, embryos, sperm). This work has shown that an important thermal variable is the cooling rate (change in temperature per unit time) during freezing. The correlation between cell survival and cooling rate is an "inverse U" shape. Cell survival is greatest for the cooling rate at the peak of the inverse "U", and destruction increases above or below this optimal cooling rate for survival. However, different types of cells have different optimal cooling rates for survival. This difference is associated with the structure and mass transfer properties of the cell membrane and the size of the cells. These general findings are incorporated in Mazur's "two factor" theory, which explains how cooling rates relate to cellular damage.

Mazur proposed that since the probability of an ice crystal forming at any temperature is a function of volume during freezing of cells in a cellular suspension, ice forms first in the much larger extracellular space, before each individual cell freezes. Since ice does not incorporate solutes, the ice that forms in the extracellular space rejects the solutes into the remaining unfrozen solution. The concentration of solutes in the extracellular solution consequently increases. The small volume of intracellular solution results in a correspondingly low probability for ice nucleation to occur inside the cell. Therefore, with sufficiently low cooling rates, the intracellular solution can remain supercooled and unfrozen, when the extracellular solution begins to freeze and exclude solutes. Under these circumstances, the unfrozen cells become surrounded by a hypertonic solution. To equilibrate the difference in chemical potential between the intracellular and the extracellular solution, water passes through the cell membrane, which is permeable to water but impermeable to ions and other organic solutes. Therefore, as the temperature of the solution is lowered and additional ice forms in the extracellular solution, water leaves the cell to equilibrate the intracellular and the extracellular concentration, and the cell dehydrates and shrinks. The intracellular solution remains unfrozen and become hypertonic, causing chemical damage involving denaturation of intracellular proteins. Since chemical damage is a function of time and temperature, the damage increases with lower cooling rates. Because water transport is a rate dependent process, faster freezing with higher cooling rates decreases the amount of time a cell is exposed to the chemically damaging conditions and increases survival. This explains the increase in cell viability with an increase in cooling rate toward an optimum. However, increasing the cooling rate also results in a more rapid decrease in temperature. The unfrozen water in cells therefore experience a greater thermodynamic supercooling. The supercooled intracellular solution is thermodynamically unstable, and after reaching a certain value it nucleates and freezes. It is thought that the intracellular ice formation damages cells. The probability of intracellular ice formation increases with increasing cooling rate, and consequently the survival of frozen cells decreases with increasing cooling rate.

These two modes of damage, chemical at low cooling rates and intracellular ice formation at high cooling rates, form the basis of the "two factor" theory of cellular damage proposed by Mazur. Survival of cells is optimal during freezing with thermal conditions in which these two conflicting modes of damage are minimized.

Based on this fundamental knowledge of the effects of thermal variables on survival of frozen cells, it has been proposed that controlling the cooling rates during freezing can be used to design optimal cryosurgical protocols. While cryosurgical procedures can be optimized to take advantage of the effects of thermal variables (e.g. cooling rates) on the outcome of freezing, this is difficult to accomplish when the means for control are limited by the number and restricted placement of the cryosurgical probes. With normally only five cryosurgical probes, it is very difficult to control the outcome of cryosurgical procedures through control of thermal history during freezing.

Chemical compounds exist that can protect cells from damage during freezing. These compounds, usually referred to as cryoprotective or cryophylactic agents, are used in cryobiology for protecting cells and organs for preservation by freezing outside a live body.

In 1948, Polge, Smith and Parkes discovered that spermatozoa can be protected from freeze damage by the addition of glycerol. Subsequent studies have shown that compounds such as ethylene glycol, dimethyl sulfoxide, polyethylene glycol, polyvinyl pyridine and others have the ability to protect cells from freeze damage. There are two mechanisms by which cryoprotective agents protect cells from freeze damage. One is intracellular with compounds that protect cells from freeze damage by penetrating into the cells. Examples of such compounds are glycerol and dimethyl sulfoxide. The other is extracellular with compounds that protect the cells from the exterior. An example of such compound is polyvinyl pyridine. With the intracellular mechanism, the compound replaces the water in the cell, and consequently reduces both the reduction of the cell volume during slow freezing by remaining in the cells as the cell dehydrates, as well as the probability of intracellular nucleation during rapid freezing. The protection afforded by the intracellular cryoprotectants is concentration dependent, increasing with the concentration until a maximal value is reached where the chemotoxic effects of the cryoprotectants become damaging to the cells. The extracellular protecting compounds presumably protect the cell by interacting with the outer cell membrane and also by inhibiting the rate of water dehydration. FIG. 1 illustrates the effects of intracellular and extracellular cryoprotective agents on cells during cryosurgery.

An object of the present invention is to develop a cryosurgery method and apparatus, which protects desirable tissue from damage during cryosurgery of unwanted tissue.

SUMMARY OF THE INVENTION

In one aspect, the invention features a method for protecting tissue in-vivo from damage during cryosurgery. According to the method, a cryoprotective agent is introduced to a tissue region to be protected in an amount sufficient to protect the tissue from damage, and cryosurgery is performed on the tissue to be destroyed. An appropriate concentration of the cryoprotective agent is determined either by calculation or by experimentation. In one embodiment, the cryoprotective agent is introduced prior to cryosurgery. In another embodiment, the cryoprotective agent is introduced during cryosurgery. In either embodiments, cryosurgery may begin to freeze tissue away from a protected region toward the protected region or alternatively from the protected region toward tissue away from the protected region. In still another embodiment, the method further includes the step of imaging the process of introducing the cryoprotective agent to a tissue to be protected and the process of cryosurgery. Examples of suitable imaging techniques include ultrasound imaging and magnetic resonance imaging.

In another aspect, the invention features a composition of matter for protecting tissue in-vivo from damage during cryosurgery. The composition includes a physiologically compatible solution and a cryoprotective agent. The cryoprotective agent protects the tissue from damage during cryosurgery. Examples of the cryoprotective agent include glycerol, dimethyl sulfoxide, ethylene glycol, and polyethylene glycol.

In still another aspect, the invention features an apparatus for introducing a cryoprotective agent to a tissue area in-vivo to be protected during cryosurgery. The apparatus includes a tubular device, which has an inner tube and an outer tube. The outer tube has a porous region. The cryoprotective agent is delivered to the tissue area through the porous region. The cryoprotective agent circulates through the device by entering the device through the outer tube and exiting through the inner tube. In another embodiment, the cryoprotective agent circulates through the device by entering the device through the inner tube and exiting the device through the outer tube.

In still another aspect, the invention features a cryosurgery apparatus. The apparatus includes a device for introducing a cryoprotective agent into a tissue region to be protected, and a cryosurgical probe. The cryosurgical probe is connected to a source of cryogen. In one embodiment, the device for introducing the cryoprotective agent is sized and shaped to pass through a urethra for delivering the agent to a prostate, and the cryosurgical probe is capable of destroying prostate tumor.

BRIEF DESCRIPTION OF THE DRAWINGS

The foregoing and other objects, features and advantages of the present invention, as well as the invention itself, will be more fully understood from the following description of preferred embodiments, when read together with the accompanying drawings, in which.

DETAILED DESCRIPTION OF THE INVENTION

Figure 1:
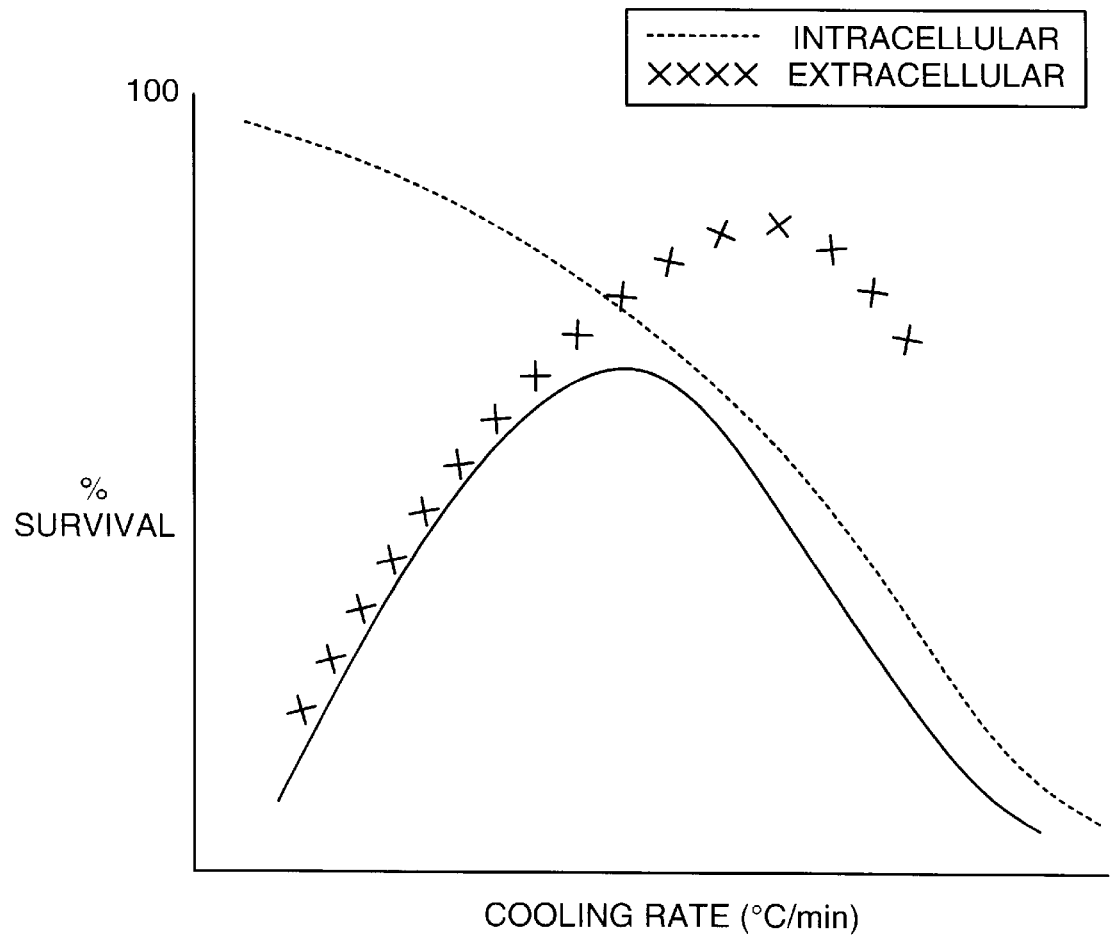
FIG. 1 illustrates effects of intracellular and extracellular cryoprotective agents on cells during cryosurgery.
Figure 2:
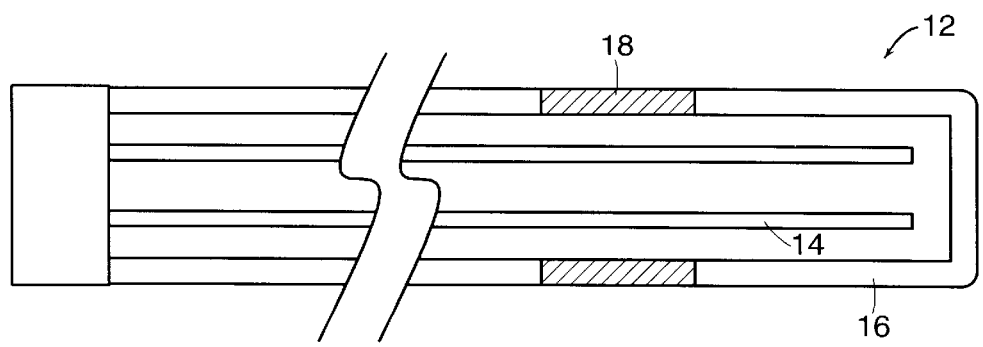
FIG. 2 shows a cross section of one embodiment of an apparatus for introducing a cryoprotective agent.

Referring to FIG. 2, an apparatus for introducing a cryoprotective agent to a tissue area to be protected from damage during cryosurgery includes a tubular device 12 with an inner tube 14 and an outer tube 16. In one embodiment, the cryoprotective agent is supplied to the tissue through the outer tube 16 and removed through the inner tube 14. A vacuum is applied to the inner tube 14 to generate circulation of the cryoprotective agent. In another embodiment, the cryoprotective agent is delivered to the tissue through the inner tube 14 and removed from the tissue through the outer tube 16. In this embodiment, vacuum is applied to the outer tube 16. In both embodiments, the outer tube 16 has a porous regions 18. The porous region 18 perfused with the cryoprotective agent contacts and delivers the cryoprotective agent to the tissue area.

Figure 3:
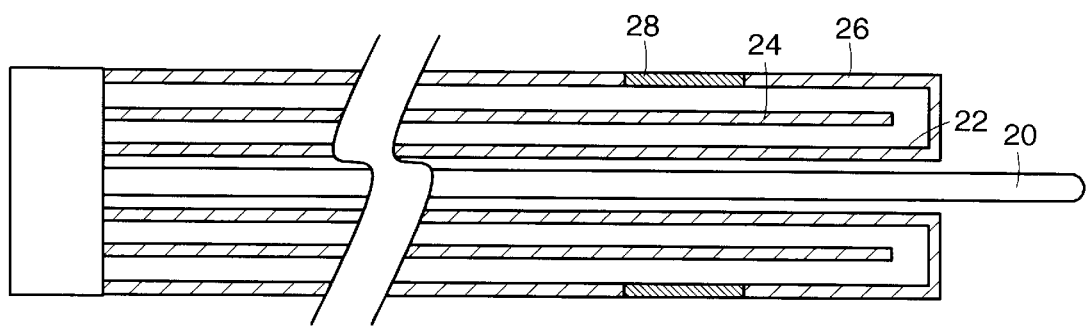
FIG. 3 shows a cross section of one embodiment of a cryosurgery apparatus.

In another embodiment, the apparatus for introducing a cryoprotective agent includes a closed circulation system (not shown). The closed system includes a reservoir of cryoprotective agent and a pump which continuously circulates the agent. In still another embodiment, the apparatus includes three tubes 22, 24, 26, and a cryosurgical probe 20 is disposed in the inner most tube 22, as shown in FIG. 3. The cryoprotective agent circulates through the apparatus via tubes 24 and 26. In one detailed embodiment, the apparatus is sized and shaped to deliver the cryoprotective agent to a prostate tissue. The tubular device is small enough to pass through a urethra and may be long enough that a distal end of the tubular device reaches a bladder. The porous region 28 is positioned along the outer tube 26 to contact the prostate when the device is inserted inside a urethra.

The apparatus for introducing the cryoprotective agent may be used with a cryosurgical probe during cryosurgery. The cryosurgical probe may be any conventional cryosurgical probe capable of destroying unwanted tissue by freezing. The cryosurgical probe, for example, may include a Joule-Thompson expansion chamber inside the probe to cool the probe. The cryosurgical probe, for example, may be connected to an external source of cryogen. In certain procedures, multiples cryosurgical probes may be employed in performing cryosurgery.

The cryoprotective agent protects tissue from freeze damage during cryosurgery. Examples of suitable cryoprotective agents include glycerol, dimethyl sulfoxide, ethylene glycol, and polyethylene glycol. The cryoprotective agent can be delivered to a tissue region along with a physiologically compatible solution. Examples of physiologically compatible solutions include, distilled water, physiological saline, Dulbecco's solution, Phosphate buffer solution, and Krebs solution.

The invention also features a method for protecting tissue from freeze damage during cryosurgery. The method may be practiced with the apparatuses of FIGS. 2 or 3, or may be practiced with other suitable apparatuses. According to the method, a cryoprotective agent is introduced to a tissue region to be protected in an amount sufficient to protect the tissue from damage during cryosurgery. Cryosurgery is performed on the tissue to be destroyed. An appropriate amount of cryoprotective agent to be delivered can be determined by calculation or by experimentation. In one embodiment, the cryoprotective agent is introduced in a gradually increasing amount to avoid damage caused by the osmotic effect it has on cells.

Appropriate amount of cryoprotective agent can be calculated using the following mathematical model. The following example illustrates distribution of a cryoprotective agent in a tissue. Tissue perfused by blood with a volumetric flow rate of w ($m^3$blood/($m^3$tissue×sec)) is brought into good mass transfer contact with a solution containing a cryoprotective agent at a concentration. The bio-mass transfer equation in live biological tissue can be solved to obtain the cryoprotective agent concentration distribution in the tissue as a function of time. This information can be used to provide proper protection of desirable parts of the tissue from freezing damage.

The bio-mass transfer equation takes the form:

$$\frac{\partial c}{\partial t} = D\frac{\partial^2 c}{\partial x^2} - wc$$

where, c is concentration, t is time, D is diffusivity, x is a Cartesian space coordinate and w is volumetric flow rate of blood.

This equation has to be solved subject to the following initial and boundary conditions.

$$c(x,0)=c(\infty,t)=0$$

$$c(0,t)=c_0$$

The solution to this equation, which gives the cryoprotective agent concentration in the tissue as a function of time and in space is given below and can be verified by substitution.

$$c(x,t) = \frac{1}{2}c_0\left[\exp\left(-x\sqrt{\frac{w}{D}}\right)\cdot erfc\left(\frac{x}{2\sqrt{D\cdot t}} - \sqrt{w\cdot D}\right) + \right.$$

-continued $$\exp\left(x\sqrt{\frac{w}{D}}\right) \cdot \operatorname{erfc}\left(\frac{x}{2\sqrt{D \cdot t}} - \sqrt{w \cdot D}\right)\Bigg]$$

Mathematical models such as this one, as well as experiments, can be used to provide information about the distribution of cryoprotective agents in tissue for appropriate protection at desired locations.

In one embodiment, cryosurgery is performed after the protected tissue region is perfused with the cryoprotective agent. Alternatively, cryoprotective agent can be introduced during cryosurgery. In one embodiment, freezing starts from near the protected tissue region and moves towards unprotected regions. The result of this embodiment is creation of a region that is intact surrounded by a region that is destroyed. In another embodiment, freezing starts from an area away from the protected area and moves toward the protected region. The result of this latter embodiment is creation of a destroyed region surrounded by an area that is intact or creation of a destroyed region which incorporates an intact region.

In another embodiment, the process of introducing the cryoprotective agent to a protected tissue region and/or cryosurgery is monitored using an imaging technique. Examples of suitable imaging techniques include ultrasound imaging and magnetic resonance imaging.

Experiments

Experiment 1: Freezing of Prostate Cancer Tissue Slices

Human prostate tissue obtained from resection biopsies of the normal and the diseased part of human prostates can be used to perform the following experiment. The tissues to be studied are immersed in a preserving solution (Hank's balanced saline solutions (Sigma) to which penicillin G, streptomycin and gentamicin are added) and transported on ice. The tissues are sliced to a thickness of about 100–300 $\mu$m using a microtome, placed on a regular glass microslide, and covered with a coverslip. The tissues are frozen on a directional solidification stage with controlled thermal variables. The tissue slices are frozen in physiological saline solution with and without 2 mols of dimethyl sulfoxide. The process of freezing is imaged with light microscopy. After freezing and thawing, the viability of the cells is determined using a two dye fluorescent test. The two color viability assay analyzes the viability of tissue slices.

Controls prior to freezing as well as tissue slices after thawing are first incubated in 250 $\mu$l of 10 $\mu$M EthD-1 in Dulbecco's phosphate buffer at 37° C. for 30 minutes with gentle rocking. This dye fluoresces red upon binding to nucleic acids of compromised cells. After 30 minutes, 250 $\mu$l of 10 $\mu$M of SYTO™-16, a nucleic acid stain from Molecular Probes Inc. (Eugene, Oreg.) is added to the mix. While being gently rocked, it is incubated at 37° C. for an additional 60 minutes. The SYTO™-16 dye is a cell permeating dye with very high penetration ability and high affinity for nucleic acids. This dye fluoresces with a very bright green color (about 525 nm) upon binding to nucleic acids. EthD-1 and SYTO-16 do not interfere with each other's binding sites. It is possible to distinguish the live cells from the dead cells in the tissue, as the dead cells fluoresce both in green and red, while the live cells fluoresce in green only. After freezing with 1° C./min to −35° C., the tissues with the cryoprotective agent will show a significantly higher viability than those frozen without the agent.

Experiment 2: Animal Experiments

The following experiment can be performed on dogs. Prostate of one male dog is interstitially injected with a solution of physiological saline without a cryoprotective agent, and prostate of another male dog is injected with a solution of saline with a cryoprotective agent (2M, Me$_2$SO). The amount of Me$_2$SO used should be sufficient to saturate the dog's prostate at that concentration. The prostates of the two dogs are frozen under ultrasound guidance with similar thermal conditions, and the dogs are sacrificed. The prostates are removed, and a biopsy is performed to compare the tissue structure frozen with and without the cryoprotective agent. The viability of the prostate cells are determined using the two dye test discussed in Experiment 1. The results will show that in the presence of the cryoprotective agent, the tissue damage is significantly less extensive than it is without the cryoprotective agent. In the presence of the cryoprotective agent, the amount of tissue damaged will also be much less than the amount of tissue which appeared to be frozen under ultrasound imaging.

Experiment 3: Animal Experiments

Figure 4:
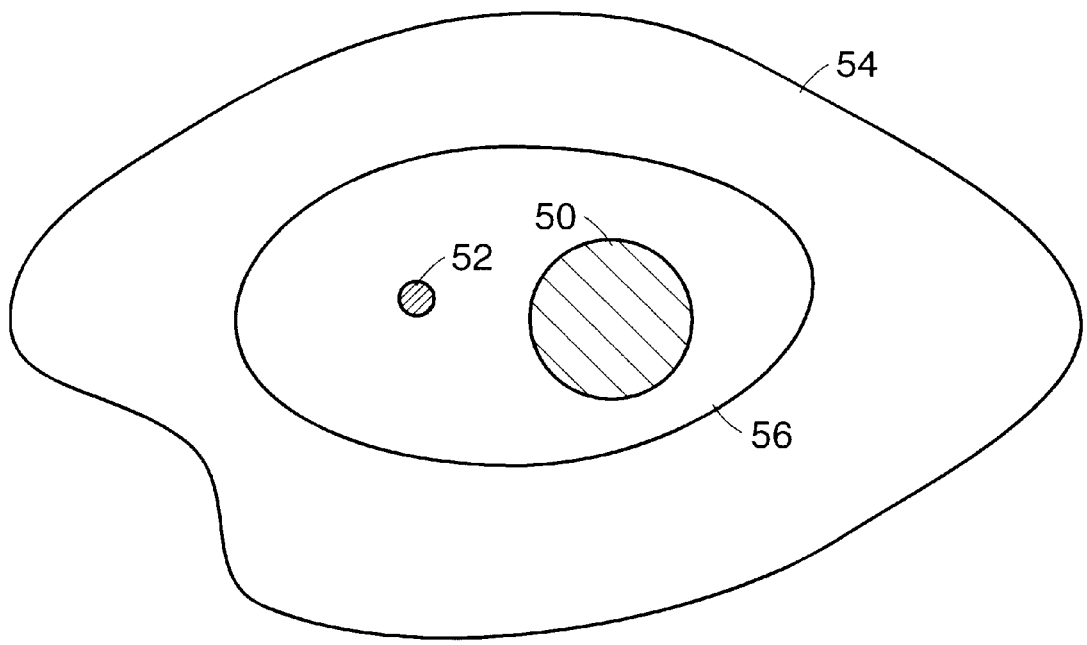
FIG. 4 shows a cross section of a liver perfused with a cryoprotective agent and subjected to cryosurgery.

An experiment can be performed to illustrate the ability of this technology to protect desirable tissue from freezing, when the freezing is done from outside the desirable tissue. An experiment may be performed with a pig, in which its liver is exposed via a midline incision of the abdomen. The liver is imaged with ultrasound, and a particular location is identified to be used as a protected region not to be destroyed during cryosurgery. Referring to FIG. 4, a syringe with a solution of physiological saline with 1.5 M glycerol is inserted into the protected region 50, and the solution is injected to that site 50. Prior to the injection, calculations may be made to ensure that desired extent of protection is afforded, both in terms of space and time. A cryosurgical probe is introduced into an area 52 of the liver, adjacent the protected region 50, and the liver 54 is frozen under ultrasound guidance until the protected region 50 is completely surrounded by the freezing interface 56. After freezing, the liver 54 is removed, a cross section of the liver 54 is taken, and a slice normal to the cryosurgical probe puncture 52 is taken. Viability of the liver slice is evaluated with the fluorescent dies discussed above. The results would indicate that the liver around the region injected with the cryoprotective compound 50 survives freezing as illustrated schematically in FIG. 4.

Experiment 4: Animal Experiments

Figure 5:
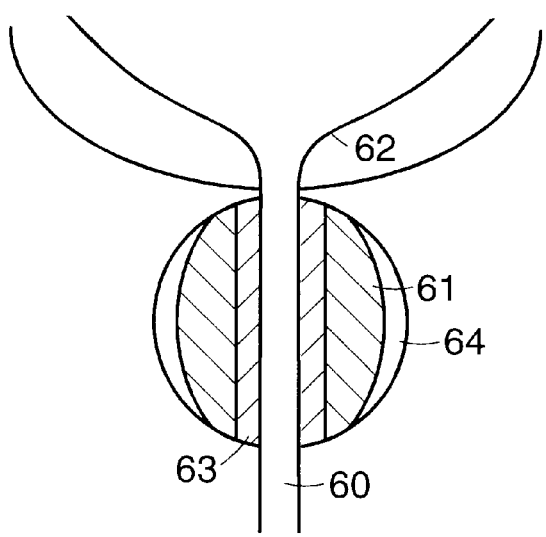
FIG. 5 illustrates effects of prostate cryosurgery performed with a cryoprotective agent.

An experiment has been performed to demonstrate that it is possible to freeze through a desirable tissue protected with cryoprotective agents, while protecting that tissue. The experiment was performed with two dogs. After anesthesia, a dog's urethra 60 was cannulated with an apparatus for introducing a cryoprotective agent. The apparatus, which consists of a simple open tube connected to a container of Me$_2$SO was introduced to the dog's bladder 62 through its urethra 60. The tube was perfused with a solution of 2M, Me$_2$SO in buffered physiological solution for 15 minutes to deliver the agent to the dog's prostate 64. The tube was removed, and a liquid nitrogen cryosurgical probe was introduced to the prostate through the urethra 60. The prostate 64 was frozen under ultrasound monitoring from the urethra 60 outward. After freezing, the prostate was removed and resected normal to the urethra. As illustrated in FIG. 5, prostate near the urethra 63, which is perfused with a cryoprotective agent was protected from freeze damage, while prostate away from the urethra 61 was destroyed during cryosurgery. Viability studies with fluorescent showed that despite being frozen, the prostate area near the urethra 63, survived freezing, while inner regions of the prostate 61 were destroyed.

Equivalents

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method of protecting tissue in-vivo from damage during cryosurgery comprising:

introducing a cryoprotective agent to a tissue for protecting the tissue from damage during cryosurgery; and performing cryosurgery of a tissue to be destroyed.

2. The method of claim 1 further comprising determining an appropriate concentration of the cryoprotective agent to introduce to the tissue to be protected.

3. The method of claim 2 wherein determining an appropriate concentration of the cryoprotective agent is by calculation or by experimentation.

4. The method of claim 1 wherein introducing a cryoprotective agent to a tissue comprises introducing the cryoprotective agent in a gradually increasing amount.

5. The method of claim 1 wherein introducing a cryoprotective agent to a tissue comprises introducing the cryoprotective agent prior to cryosurgery, and performing cryosurgery of the tissue to be destroyed comprises freezing from an area of the tissue away from a protected region toward the protected region.

6. The method of claim 1 wherein introducing a cryoprotective agent to a tissue comprises introducing the cryoprotective agent during cryosurgery, and performing cryosurgery of the tissue to be destroyed comprises freezing from an area of the tissue away from a protected region toward the protected region.

7. The method of claim 1 wherein introducing a cryoprotective agent to a tissue comprises introducing the cryoprotective agent prior to cryosurgery, and performing cryosurgery of the tissue to be destroyed comprises freezing from a region in a protected region toward an area of the tissue away from the protected region.

8. The method of claim 1 wherein introducing a cryoprotective agent to a tissue comprises introducing the cryoprotective agent during cryosurgery, and performing cryosurgery of the tissue to be destroyed comprises freezing from a region in a protected region toward an area of the tissue away from the protected region.

9. The method of claim 1 further comprising imaging the process of introducing the cryoprotective agent to a tissue and the process of cryosurgery.

10. The method of claim 9 wherein imaging comprises imaging with ultrasound imaging or magnetic resonance imaging techniques.

* * * * *